(12) United States Patent
Park et al.

(10) Patent No.: US 11,951,060 B2
(45) Date of Patent: Apr. 9, 2024

(54) FOOT STRETCHING AND DIAGNOSIS DEVICE, AND METHOD FOR CALCULATING STIFFNESS OF FOOT

(71) Applicant: Korea Advanced Institute of Science and Technology, Daejeon (KR)

(72) Inventors: Hyungsoon Park, Daejeon (KR); Yusung Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 758 days.

(21) Appl. No.: 16/625,067

(22) PCT Filed: Dec. 19, 2019

(86) PCT No.: PCT/KR2019/018063
§ 371 (c)(1),
(2) Date: Sep. 10, 2020

(87) PCT Pub. No.: WO2020/251126
PCT Pub. Date: Dec. 17, 2020

(65) Prior Publication Data
US 2021/0353492 A1    Nov. 18, 2021

(30) Foreign Application Priority Data

Jun. 11, 2019 (KR) .................. 10-2019-0068969

(51) Int. Cl.
*A61H 1/02* (2006.01)
(52) U.S. Cl.
CPC ..... *A61H 1/0266* (2013.01); *A61H 2001/027* (2013.01); *A61H 2201/1215* (2013.01);
(Continued)

(58) Field of Classification Search
CPC ............ A61H 1/0266; A61H 2001/027; A61H 2201/164; A61H 2201/1642;
(Continued)

(56) References Cited

U.S. PATENT DOCUMENTS

2007/0037672 A1 * 2/2007 Nakanishi .......... A63B 21/0428
482/121

FOREIGN PATENT DOCUMENTS

CN    104013408 A  *  9/2014
JP    2004-089616 A     3/2004
(Continued)

OTHER PUBLICATIONS

English Machine Translation of JP-2004089616-A provided by Espacenet (Year: 2004).*

(Continued)

*Primary Examiner* — Joseph D. Boecker
*Assistant Examiner* — Brian T Khong
(74) *Attorney, Agent, or Firm* — Maier & Maier, PLLC (57) ABSTRACT

A foot stretching/checkup device includes: a motor unit; a footrest unit including a lower footrest configured to be rotated about a first rotation axis, an upper footrest configured to be rotated about a second rotation axis and a connecting member connecting the upper footrest and the lower footrest; and a coupling unit including an arm portion rotated by the motor unit and a rotary coupler coupled to the upper footrest. The upper footrest is configured to be rotated by a predetermined angle about the second rotation axis by the rotation of the arm portion. The lower footrest is configured not to be rotated about the first rotation axis by rotation of the arm portion until the upper footrest is rotated by the predetermined angle.

14 Claims, 8 Drawing Sheets

(52) U.S. Cl.
CPC ............... *A61H 2201/1642* (2013.01); *A61H 2201/5069* (2013.01)

(58) Field of Classification Search
CPC .... A61H 2201/1215; A61H 2201/5069; A61H 2201/5064; A61H 2205/12; A61H 2205/125; A61H 2203/0437; A61H 2203/0406; A61H 2203/0431; A61H 2203/0462; A61H 2230/60
See application file for complete search history.

(56) References Cited

FOREIGN PATENT DOCUMENTS

| | | | |
|---|---|---|---|
| JP | 2004089616 A | * | 3/2004 |
| JP | 2005013483 A | * | 1/2005 |
| JP | 3107678 U | | 2/2005 |
| JP | 2007-325903 A | | 12/2007 |
| KR | 20150058691 A | * | 5/2015 |
| KR | 10-1556477 B | | 10/2015 |
| KR | 10-2016-0145379 A | | 8/2017 |

OTHER PUBLICATIONS

English Machine Translation of CN-104013408-A provided by Espacenet (Year: 2014).*
English Machine Translation of KR-20150058691-A provided by Espacenet (Year: 2015).*
English Machine Translation of JP-2005013483-A provided by Espacenet (Year: 2005).*

* cited by examiner

FOOT STRETCHING AND DIAGNOSIS DEVICE, AND METHOD FOR CALCULATING STIFFNESS OF FOOT

TECHNICAL FIELD

The present invention relates to a foot stretching and diagnosis device, and method for calculating stiffness of foot.

This work was supported by the Korea government (MSIT) (Project unique No.: 1711193392; Project No.: 2022-0-00020-002; Government department: Ministry of Science and ICT; Research Project: Electronics and Telecommunications Research Institute R&D support; Research Project Title: Imperceptible on-skin sensor devices for musculoskeletal monitoring and rehabilitation).

BACKGROUND

Recently, various foot stretching devices have been proposed for the prevention of foot diseases and rehabilitation of a foot. As the conventional foot stretching devices, there are available a device for stretching only the ankle and a device for stretching the metatarsal joints together with the ankle. However, such conventional foot stretching devices are provided with individual stretching motors for the respective joints. That is, an ankle stretching motor and a metatarsal joint stretching motor are provided separately, which may lead to an increase in the number of components and an increase in the manufacturing cost.

In addition, the conventional foot stretching devices are used only for the purpose of stretching the joints, and do not have a function of diagnosing a foot disease.

Accordingly, a demand has existed for a device having a function of stretching a plurality of foot joints using a single motor and a function of diagnosing a foot disease.

PRIOR ART DOCUMENT

Korean Patent Application Publication No. 10-2015-0058691 (published on May 29, 2015)

SUMMARY

Embodiments of the present invention provide a foot stretching device capable of stretching two joints simultaneously using a single motor and a coupling mechanism. Furthermore, embodiments of the present invention provide a foot checkup device having a function of diagnosing a foot disease.

In accordance with an aspect of the present invention, there is provided a foot stretching/checkup device including: a motor unit; a footrest unit including a lower footrest configured to be rotated about a first rotation axis, an upper footrest configured to be rotated about a second rotation axis and a connecting member connecting the upper footrest and the lower footrest; and a coupling unit including an arm portion rotated by the motor unit and a rotary coupler coupled to the upper footrest, wherein the upper footrest is configured to be rotated by a predetermined angle about the second rotation axis by the rotation of the arm portion, and the lower footrest is configured to be rotated about the first rotation axis together with the upper footrest by rotation of the arm portion in a state in which the upper footrest has been rotated by the predetermined angle.

The angle of the lower footrest with respect to the upper footrest may be maintained when the lower footrest is rotated by the arm portion.

The upper footrest may be rotatably coupled at both side portions thereof to an upper portion of the connecting member, and the connecting member may be fixed at a lower portion thereof to both side portions of the lower footrest in a fixing-position-changeable manner.

The foot stretching/checkup device may further include a sensor to measure stiffness of a metatarsal joint of a user during rotation of the upper footrest.

The foot stretching/checkup device may further include a sensor to measure stiffness of an ankle joint of the user during the rotation of the lower footrest According to the embodiments of the present invention, it is possible to provide a foot stretching device capable of stretching two joints simultaneously using a single motor and a coupling mechanism. Furthermore, it is possible to provide a foot checkup device having a function of diagnosing a foot disease.

DETAILED DESCRIPTION

Hereinafter, configurations and operations of embodiments will be described in detail with reference to the accompanying drawings. The following description is one of various patentable aspects of the disclosure and may form a part of the detailed description of the disclosure. However, in describing the disclosure, detailed descriptions of known configurations or functions that make the disclosure obscure may be omitted.

The disclosure may be variously modified and may include various embodiments. Specific embodiments will be exemplarily illustrated in the drawings and described in the detailed description of the embodiments. However, it should be understood that they are not intended to limit the disclosure to specific embodiments but rather to cover all modifications, similarities, and alternatives which are included in the spirit and scope of the disclosure.

The terms used herein, including ordinal numbers such as "first" and "second" may be used to describe, and not to limit, various components. The terms simply distinguish the components from one another. When it is said that a component is "connected" or "linked" to another component, it should be understood that the former component may be directly connected or linked to the latter component or a third component may be interposed between the two components. Specific terms used in the present application are used simply to describe specific embodiments without limiting the disclosure. An expression used in the singular encompasses the expression of the plural, unless it has a clearly different meaning in the context.

Hereinafter, a foot stretching/checkup device according to an embodiment of the present invention will be described with reference to the accompanying drawings.

Referring to FIGS. 1 to 5, the foot stretching/checkup device 100 according to an embodiment of the present invention includes a motor unit 10, a footrest unit 20, a coupling unit 30, a support unit 40 and a controller 90. In the subject specification, the foot stretching/checkup device 100 may be interchangeably referred to as a foot stretching device or a foot checkup device depending on the usage and use aspect thereof.

The motor unit 10 includes a motor and a motor rotation shaft. The motor provides a rotational driving force, and the motor rotation shaft is a rotation shaft rotated by the motor.

The footrest unit 20 includes an upper footrest 21, a lower footrest 22, and connecting members 23 that connect the upper footrest 21 and the lower footrest 22.

In the present embodiment, the connecting members 23 may be provided in a pair on the right and left sides. When the connecting members 23 are erected, the lower portions of the connecting members 23 may be fixed to both side portions of the lower footrest 22, and the upper portions of the connecting members 23 may support both side portions of the upper footrest 21. The lower footrest 22 and the upper footrest 21 may be referred to as a first footrest 22 and a second footrest 21, respectively. The connecting members 23 are fixed so that the fixing position thereof with respect to the lower footrest 22 is changeable. By changing the fixing position of the connecting members 23, it is possible to adjust the distance between the upper footrest 21 and the lower footrest 22 depending on the size of a user's foot.

For example, a slit 23a extending in the longitudinal direction of each of the connecting members 23 may be formed in the lower portion of each of the connecting members 23. The connecting members 23 are fixed to both side portions of the lower footrest 22 by coupling fixing mechanisms 24 to both side portions of the lower footrest 22 through the slits 23a.

The fixing mechanisms 24 are configured to be tightened and loosened. The connecting members 23 is coupled to the lower footrest 22 by tightening the fixing mechanisms 24, and the connecting members 23 is decoupled from the lower footrest 22 by loosening the fixing mechanisms 24, so that the fixing positions of the connecting members 23 can be changed. In this state, the distance between the upper footrest 21 and the lower footrest 22 is adjusted according to the foot size of the user. Thereafter, by tightening the fixing mechanisms 24, the upper footrest 21 and the lower footrest 22 are coupled through the connecting members 23 in a state in which they are spaced apart from each other by a predetermined distance.

The support unit 40 includes a pair of side support portions 40a and 40b and a lower support portion 40c.

The lower footrest 22 has a substantially "L"-like cross section so that the rear portion of the user's foot can make contact with the lower footrest 22. That is, the lower footrest 22 is composed of a horizontal plate extending in the horizontal direction and a vertical plate extending in the vertical direction.

The horizontal plate of the lower footrest 22 is rotatably coupled to the side support portions 40a and 40b so as to rotate about a first rotation axis X1. At this time, the rotation axis (first rotation axis X1) of the lower footrest 22 with respect to the side support portions 40a and 40b is positioned to substantially coincide with the ankle joint part of the user. The horizontal plate of the lower foot plate 22 is supported by the lower support portion 40c.

The lower footrest 22 may be configured to rotate only toward the user in the vertical position. To this end, a stopper (not shown) may be provided to prevent the lower footrest 22 from rotating toward the side opposite to the user (away from the user) in the vertical position.

The upper footrest 21 may be rotatably coupled to the upper portions of the connecting members 23 through, for example, a pair of coupling pieces 60, so as to be able to rotate toward one side (toward the user) about a second rotation axis X2. At this time, the rotation axis (second rotation axis X2) of the upper footrest 21 with respect to the connecting members 23 is positioned to substantially coincide with the metatarsal joints of the user.

The upper footrest 21 may be configured to rotate only toward the user in the vertical position. To this end, a stopper (not shown) may be provided to prevent the upper footrest 21 from rotating toward the side opposite to the user (away from the user) in the vertical position.

The coupling pieces 60 may have a configuration capable of adjusting the horizontal position of the upper footrest 21. For example, each of the coupling pieces 60 is formed in a substantially inverted "L"-like shape, and includes a horizontal portion 60a and a vertical portion 60b. A slit 61 extending in the horizontal direction is formed in the horizontal portion 60a. The coupling pieces 60 are fixed to both side portions of the upper footrest 21 by coupling fixing mechanisms 62 to both side portions of the upper footrest 21 through the slits 61. The vertical portions 60b of the coupling pieces 60 are fixed to the upper portions of the connecting members 23.

The fixing mechanisms 62 are configured to be tightened and loosened. By tightening the fixing mechanisms 62, the coupling pieces 60 are fixed to the upper footrest 21. By loosening the fixing mechanisms 62, the coupling pieces 60 are decoupled from the upper footrest 21. In this state, the upper footrest 21 is arranged at a desired horizontal position. Thereafter, the coupling pieces 60 are fixed to the upper footrest 21 by tightening the fixing mechanisms 62 through the slits 61.

The coupling unit 30 includes an arm portion 31 coupled to the motor rotation shaft of the motor unit 10, and a rotary coupler 32 coupled to one side of the upper footrest 21.

The arm portion 31 is coupled at its rear end to the motor rotation shaft of the motor unit 10 so that it can be rotated together with the motor rotation shaft during rotation of the motor rotation shaft.

At the front end portion of the arm portion 31, there is provided a contact portion 31a that makes contact with the rotary coupler 32 and presses the rotary coupler 32. The contact portion 31a of the arm portion 31 comes into contact with the lower surface of the front end portion of the rotary coupler 32 when the front end portion of the arm portion 31 is rotated upward. Thus, the contact portion 31a of the arm portion 31 may press the rotary coupler 32 to rotate the rotary coupler 32.

The rear end portion of the rotary coupler 32 is coupled to one side of the upper footrest 21. When the rotary coupler 32 is rotated due to the rotation of the contact portion 31a of the arm portion 31, the upper footrest 21 may be rotated by a predetermined angle about the second rotation axis X2 together with the rotary coupler 32.

As the upper footrest 21 is rotated, the toes of the user lying on the upper footrest 21 are bent upward to stretch the metatarsal joints.

Meanwhile, the rotary coupler 32 is in contact with the arm portion 31. The rotary coupler 32 may be rotated relative to the connecting members 23 and the arm portion 31 by the rotation of the arm portion 31. The direction in which the arm portion 31 rotates about the rotation center and the direction in which the rotary coupler 32 rotates about the rotation center may be the same. The angle at which the rotary coupler 32 rotates by the rotation of the arm portion 31 may be limited to a predetermined angle. For example, when the rotary coupler 32 is rotated by a predetermined angle so that the entire lower surface of the rotary coupler 32 makes contact with the contact portion 31a of the arm portion 31, the rotary coupler 32 stops rotating about the second rotation axis X2. While the rotary coupler 32 is rotated with respect to the connecting members 23 and the arm portion 31, the position and posture of the connecting members 23 may be kept unchanged.

Thereafter, if the arm portion 31 is further rotated by the rotation of the motor rotation shaft, the upper footrest 21, the connecting members 23 and the lower footrest 22 are integrally rotated by a predetermined angle.

In other words, while the arm portion 31 rotates up to a first rotation angle, the rotary coupler 32 rotates relative to the connecting members 23 and the arm portions 31. Thus, the position and posture of the connecting members 23 and the lower footrest 22 can be kept unchanged. Thereafter, while the arm portion 31 rotates up to a second rotation angle beyond the first rotation angle, the rotary coupler 32 does not rotate relative to the connecting members 23 and the arm portion 31. However, the upper footrest 21, the connecting members 23 and the lower footrest 22 rotate about the first rotation axis X1 with respect to the side support portions 40a and 40b.

As the lower footrest 22 is rotated about the first rotation axis X1, the ankle portion of the user lying on the lower footrest 22 is bent upward to stretch the ankle joint.

By rotating the motor rotation shaft to the opposite side, the lower footrest 22 and the upper footrest 21 are rotated in the reverse direction and returned to their original positions.

Hereinafter, an operation process of the coupling unit 30 and the footrest unit 20 of the foot stretching/checkup device according to the embodiment of the present invention will be described with reference to FIGS. 6A to 6D. FIGS. 6A to 6D are schematic diagram schematically showing the operation process of the coupling unit and the footrest unit of the foot stretching/checkup device according to the embodiment of the present invention.

Figure 1:
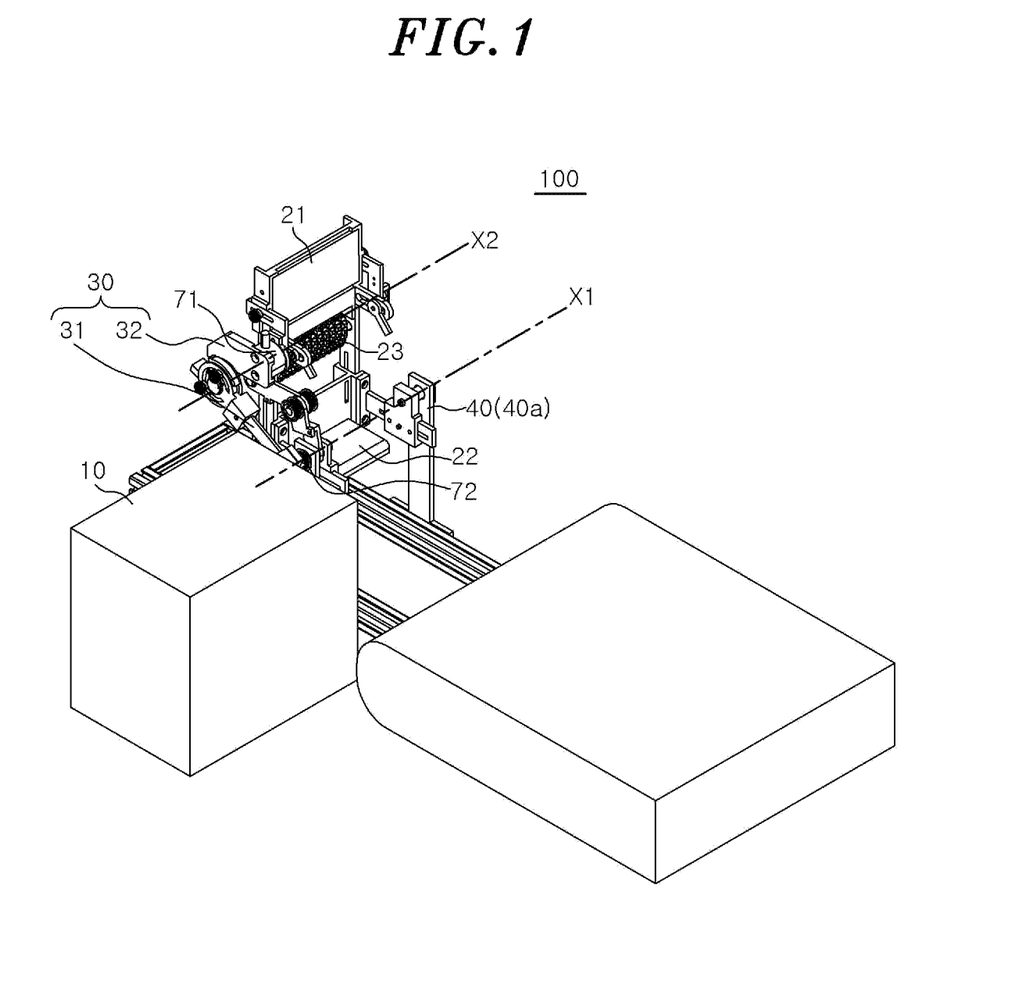
FIG. 1 is a left front perspective view of a foot stretching/checkup device according to an embodiment of the present invention.
Figure 2:
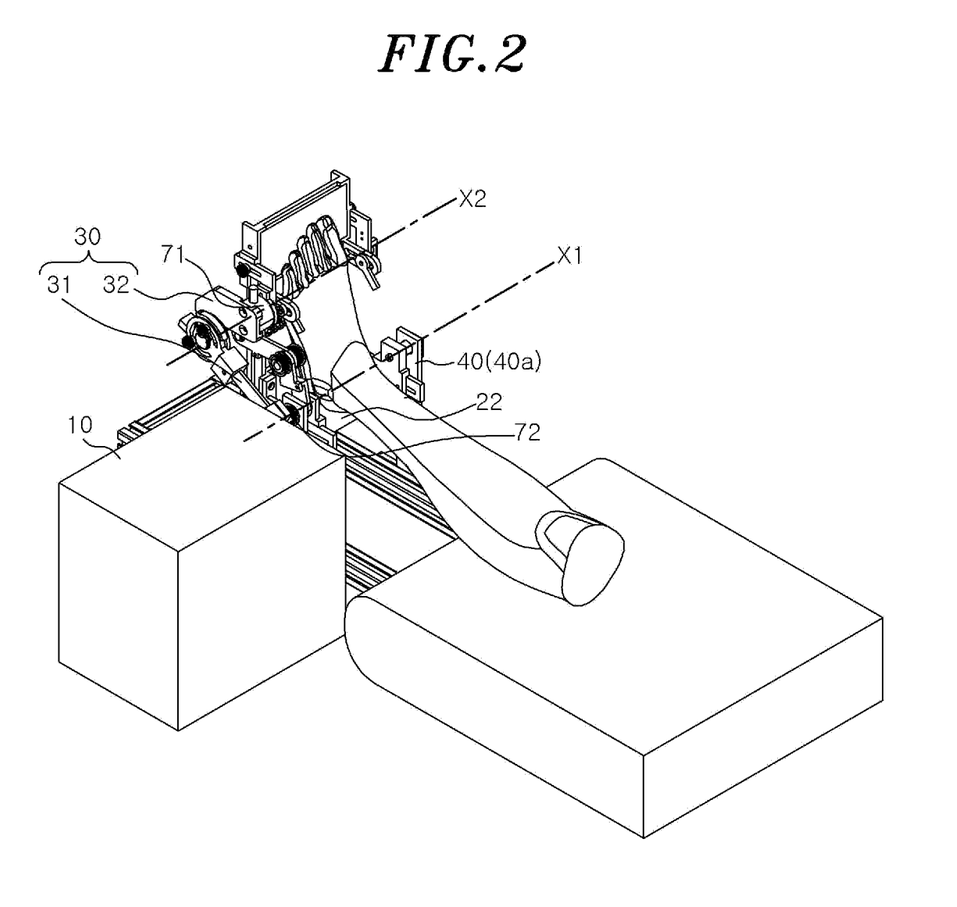
FIG. 2 is a left front perspective view illustrating a state in which a foot of a user is placed on the foot stretching/checkup device according to the embodiment of the present invention.
Figure 3:
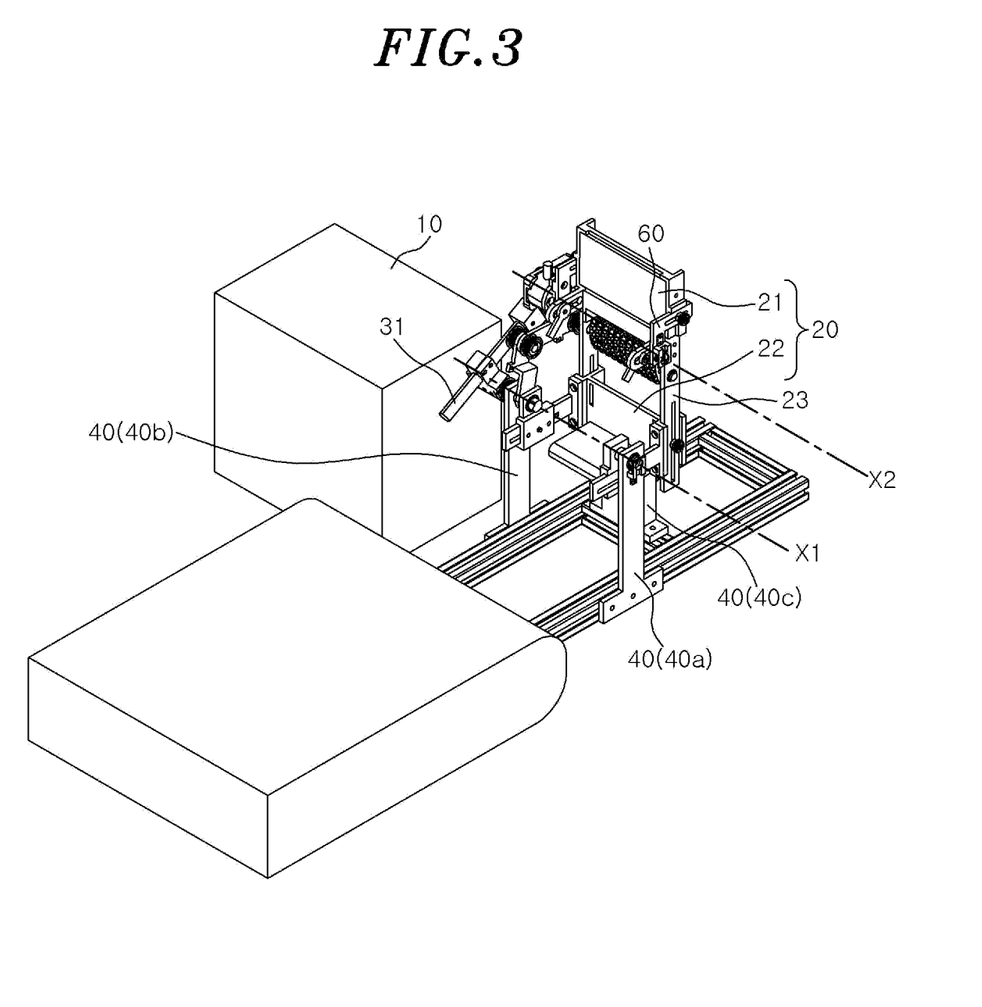
FIG. 3 is a right front perspective view of the foot stretching/checkup device according to the embodiment of the present invention.
Figure 4:
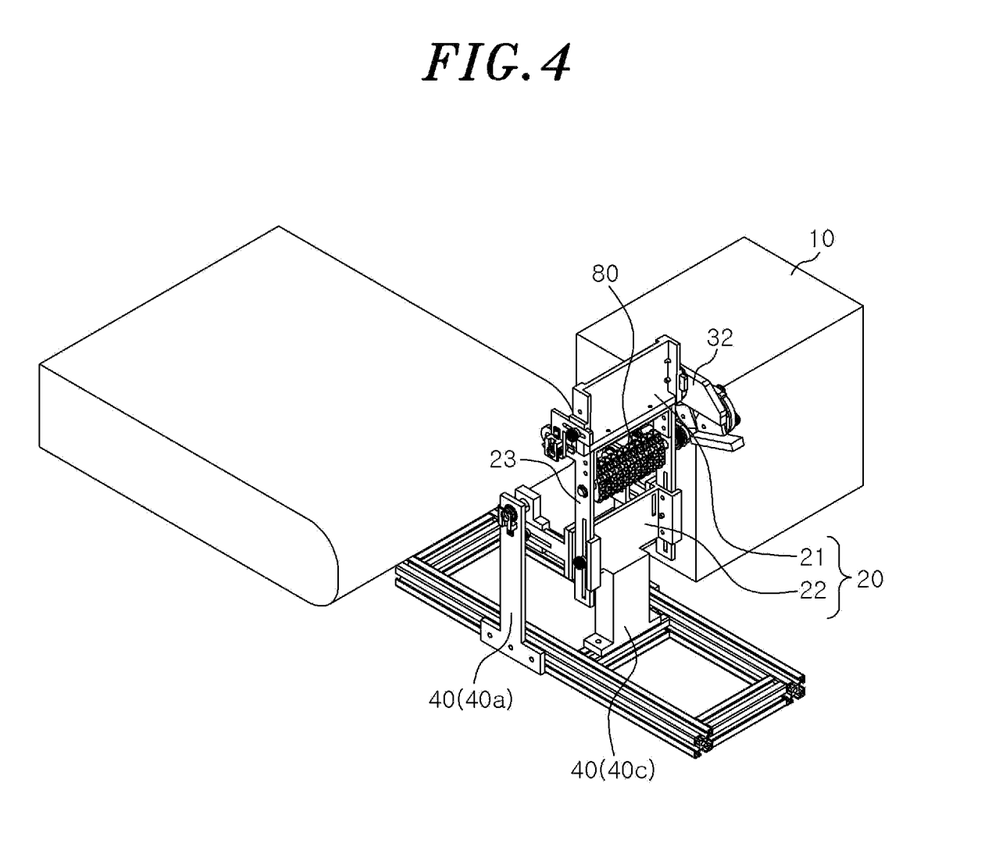
FIG. 4 is a right rear perspective view of the foot stretching/checkup device according to the embodiment of the present invention.
Figure 5:
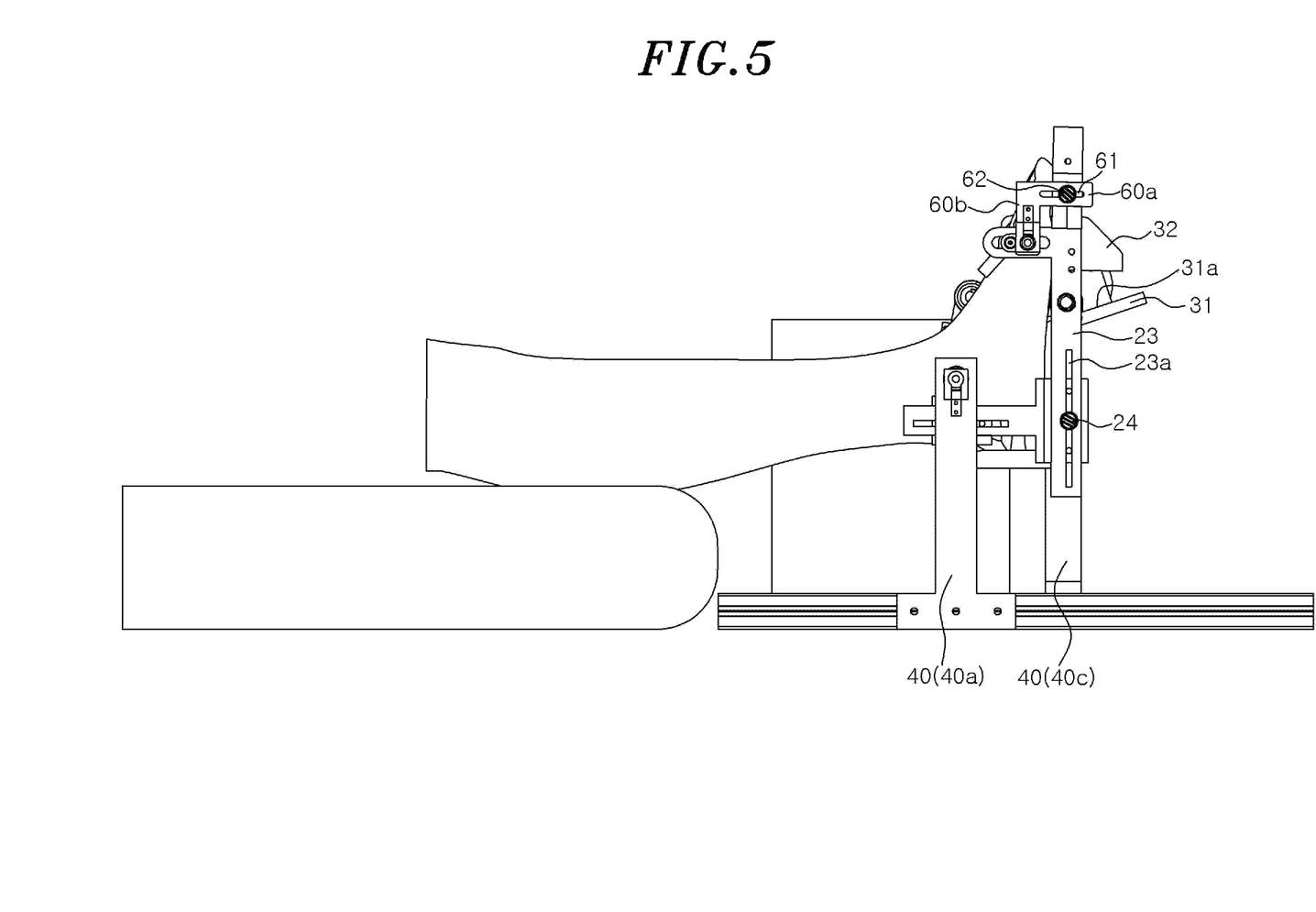
FIG. 5 is a right side view of the foot stretching/checkup device according to the embodiment of the present invention.
Figure 6A:
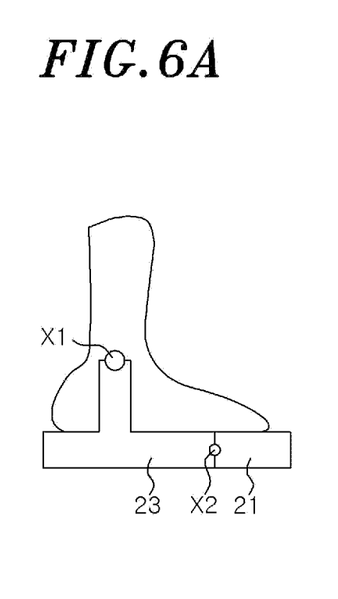
FIGS. 6A to 6D are schematic diagrams schematically showing an operation process of a coupling unit and a footrest unit of the foot stretching/checkup device according to the embodiment of the present invention.
Figure 6B:
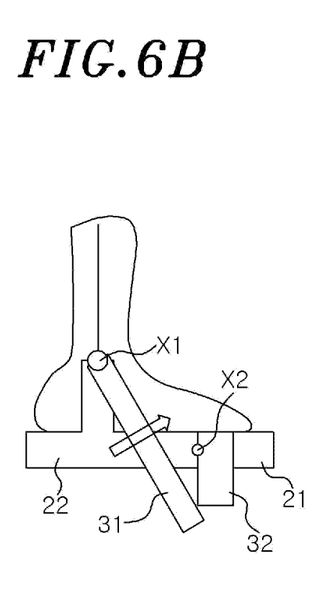

First, as shown in FIG. 6A, when the motor is operated with the user's foot placed on the footrest unit 20, the arm portion 31 is rotated so that, as shown in FIG. 6B, the contact portion 31a of the arm portion 31 comes into contact with the lower surface of the front end portion of the rotary coupler 32.

Figure 6C:
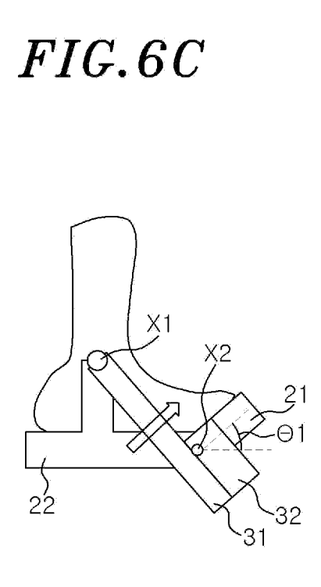

In this state, if the motor continues to operate, as shown in FIG. 6C, the rotary coupler 32 in contact with the arm portion 31 is rotated by the rotation of the contact portion 31a of the arm portion 31. The upper footrest 21 is rotated by a predetermined angle θ1 about the second rotation axis X2 together with the rotary coupler 32. Thus, the toes of the user lying on the upper footrest 21 are bent upward to stretch the metatarsal joints.

Figure 6D:
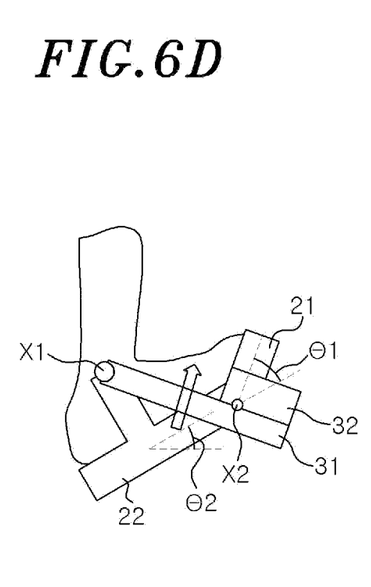

In this state, if the motor continues to operate, as shown in FIG. 6D, the rotation of the rotary coupler 32 about the second rotation axis X2 is stopped, and the upper footrest 21 and the lower footrest 22 coupled to the upper footrest 21 through the connecting members 23 are integrally rotated by a predetermined angle θ2 about the first rotation axis X1. As the lower footrest 22 is rotated about the first rotation axis X1 in this way, the ankle portion of the user lying on the lower footrest 22 is bent upward to stretch the ankle joint.

As described above, the foot stretching/checkup device 100 according to the embodiment of the present invention is capable of simultaneously stretching the metatarsal joint and the ankle joint using the single motor and the coupling mechanism.

Figure 7:
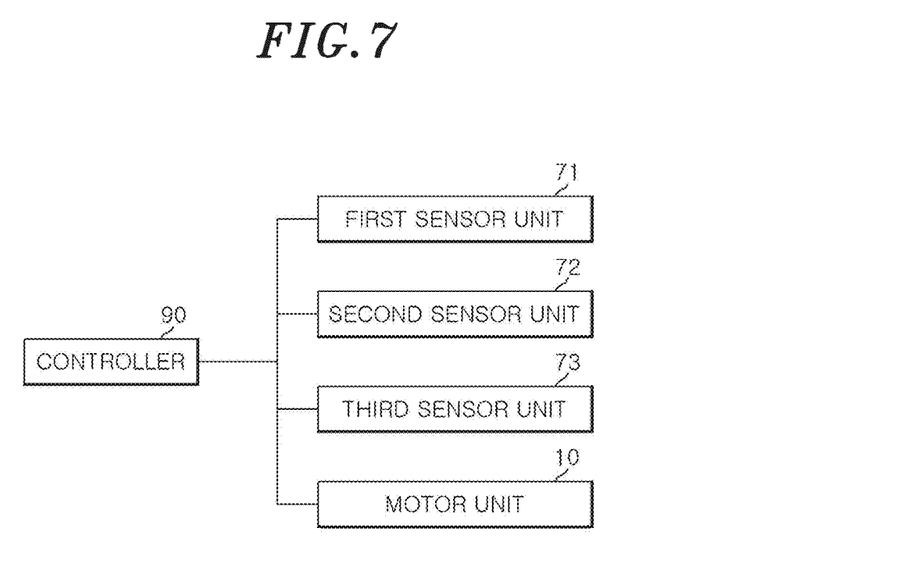
FIG. 7 is a block diagram for explaining a checkup function of the foot stretching/checkup device according to the embodiment of the present invention.

Hereinafter, a checkup function of the foot stretching/checkup device 100 according to the embodiment of the present invention will be described with reference to FIG. 7.

The foot stretching/checkup device 100 according to the embodiment of the present invention may further include a first sensor unit 71 for measuring the stiffness of the metatarsal joint of the user during rotation of the upper footrest 21, a second sensor unit 72 for measuring the stiffness of the ankle joint of the user during rotation of the lower footrest 22, and a third sensor unit 73 for measuring the stiffness of the sole of the user during rotation of an indenter 80 to be described later.

Each of the first sensor unit 71, the second sensor unit 72 and the third sensor unit 73 may include a torque sensor and an angle sensor. The first sensor unit 71 and the second sensor unit 72 may be installed on the second rotation axis X2 and the first rotation axis X1, respectively.

The controller 90 may calculate the stiffness of the metatarsal joint or the ankle joint of the user based on the rotation angle of the upper footrest 21 or the lower footrest 22 measured by the angle sensor and the torque measured by the torque sensor. The controller 90 may check whether the user has a foot disease by comparing the calculated stiffness information with pre-inputted foot disease condition information.

The controller 90 may be implemented by an arithmetic device including a microprocessor, a memory and the like. Since the implementation method is obvious to those skilled in the art, a detailed description thereof will be omitted.

In addition, the foot stretching/checkup device 100 according to the embodiment of the present invention may further include an indenter 80 rotatably supported by the connecting members 23 between the upper footrest 21 and the lower footrest 22.

The indenter 80 may be rotated by a separate motor (not shown) to press the sole of the user. The third sensor unit 73 may be provided on the rotation shaft of the indenter 80.

The controller 90 may calculate the stiffness of the sole of the foot based on the rotation angle and the torque of the indenter 80 measured by the third sensor unit 73. The controller 90 may determine presence or absence of a foot disease on the sole by comparing the calculated sole stiffness with the pre-inputted foot disease data.

Figure 8:
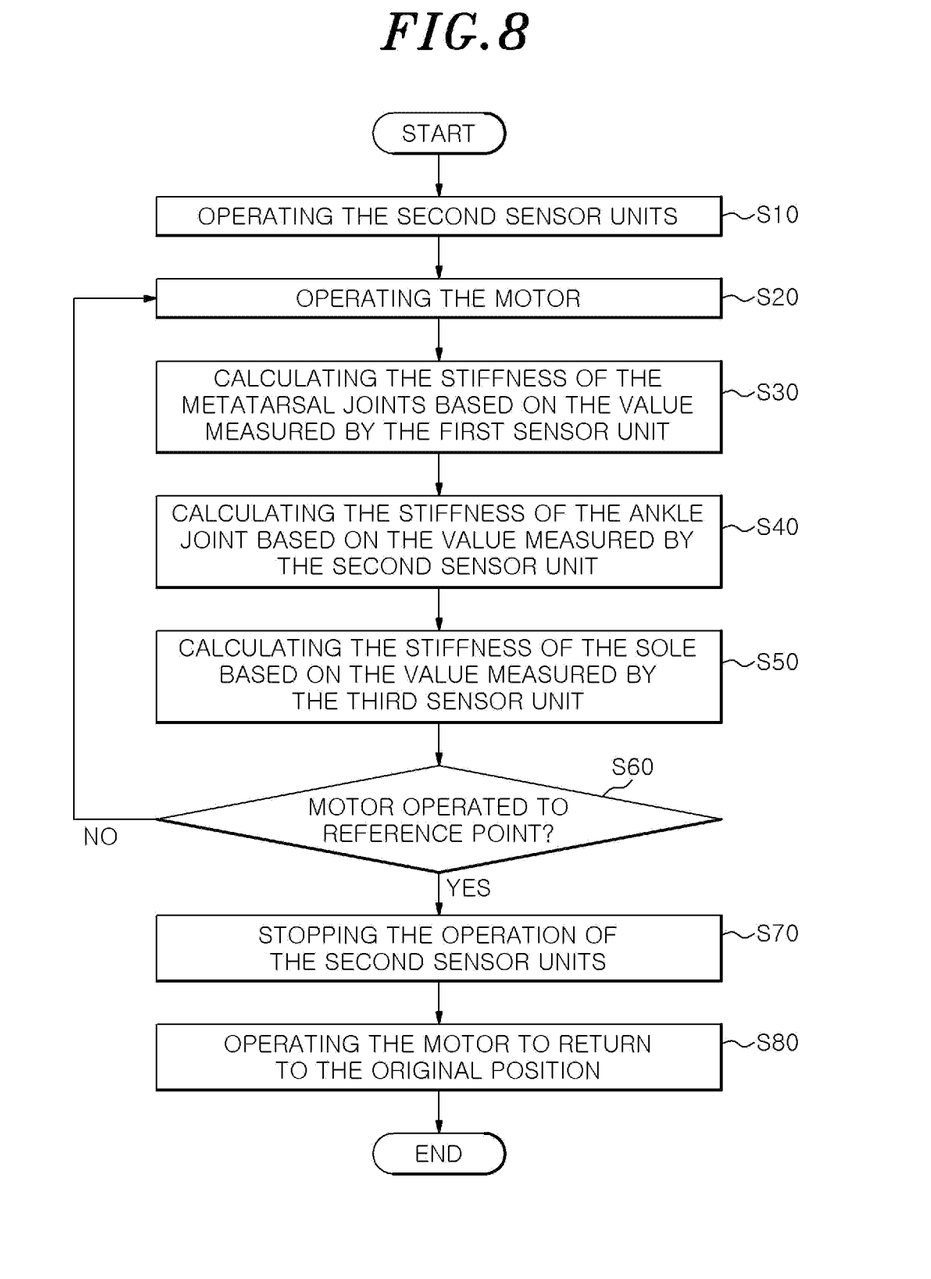
FIG. 8 is a flowchart of a foot stiffness calculation method using the foot stretching/checkup device according to the embodiment of the present invention.

Hereinafter, a foot stiffness calculation method according to an embodiment of the present invention will be described with reference to the flowchart of FIG. 8.

In the foot stiffness calculation method according to the embodiment of the present invention, first, the controller 90 operates the first sensor unit 71, the second sensor unit 72 and the third sensor unit 73 (step S10). In this case, the controller 90 may operate the first sensor unit 71, the second sensor unit 72 and the third sensor unit 73 simultaneously or sequentially, and may also operate only some of the sensor units. In this regard, the expression "operate the sensor unit" includes obtaining a measured value from the sensor unit.

Thereafter, when the motor is operated so as to rotate in one direction (step S20), the upper footrest 21 is rotated about the second rotation axis X2.

The controller 90 calculates the stiffness of the metatarsal joints of the user based on the rotation angle and the torque measured by the first sensor unit 71 in real time while rotating the upper footrest 21 (step S30).

The controller 90 may determine presence or absence of a foot disease in the metatarsal joints by comparing the calculated metatarsal joint stiffness information with the pre-inputted foot disease data.

As described above, when the motor is continuously operated while the upper footrest 21 is rotated by a predetermined angle θ1 about the second rotation axis X2, the lower footrest 22 is rotated about the first rotation axis X1 (step S40).

At this time, the controller 90 calculates the stiffness of the ankle joint of the user based on the rotation angle and the torque measured by the second sensor unit 72 in real time while rotating the lower footrest 22.

The controller 90 may determine presence or absence of a foot disease by comparing the calculated ankle joint stiffness information with the pre-stored foot disease data.

In addition, the controller 90 calculates the stiffness of the sole of the user based on the rotation angle and torque measured in real time by the third sensor unit 73 provided in the indenter 80 driven by a separate motor (step S50).

The controller 90 may determine presence or absence of a foot disease by comparing the calculated sole stiffness information with the pre-inputted foot disease data.

When the motor is rotated so that the lower footrest rotates up to a predetermined angle about the first rotation axis X1, the controller 90 determines that the motor has operated up to a reference point (step S60). If it is determined that the motor has operated up to the reference point, the controller 90 may stop the operation of the sensor units and may stop the motor from rotating in one direction (step S70). The controller 90 may stop the motor from rotating in one direction even when the values measured by the first to third sensor units 71, 72 and 73 exceeds predetermined values.

In addition, the controller 90 operates the motor so that the motor rotates in the other direction to return the upper footrest 21, the lower footrest 22 and the indenter 80 to their original positions (S80).

Thus, according to the foot stiffness calculation method according to the embodiment of the present invention, the stiffness of the metatarsal joints, the stiffness of the ankle joint and the stiffness of the sole of the foot can be calculated based on the rotation angle and torque measured by each of the first sensor unit 71, the second sensor unit 72 and the third sensor unit 73. The presence or absence of a foot disease can be determined by comparing the calculated value with the pre-stored foot disease data value.

While the invention has been shown and described with respect to the embodiments, it will be understood by those skilled in the art that various changes and modification may be made without departing from the scope of the invention as defined in the following claims.

What is claimed is:

1. A foot stretching device comprising:
   a motor unit;
   a footrest unit including a lower footrest configured to be rotated about a first rotation axis, an upper footrest configured to be rotated about a second rotation axis and a connecting member connecting the upper footrest and the lower footrest; and
   a coupling unit including an arm portion rotated by the motor unit and a rotary coupler coupled to the upper footrest,
   wherein the upper footrest is configured to be rotated by a predetermined angle about the second rotation axis by the rotation of the arm portion, and
   the lower footrest is configured not to rotate about the first rotation axis by rotation of the arm portion until the upper footrest is rotated by the predetermined angle.

2. The foot stretching device of claim 1, wherein the arm portion includes a front end portion provided with a contact portion for making contact with the rotary coupler to press the rotary coupler.

3. The foot stretching device of claim 1, wherein the upper footrest is rotatably coupled at both side portions thereof to an upper portion of the connecting member, and the connecting member is fixed at a lower portion thereof to both side portions of the lower footrest in a fixing-position-changeable manner.

4. The foot stretching device of claim 1, further comprising:
   an indenter rotatably supported by the connecting member between the upper footrest and the lower footrest.

5. The foot stretching device of claim 1, wherein the lower footrest is rotated about the first rotation axis together with the upper footrest when the upper footrest is rotated.

6. The foot stretching device of claim 5, wherein the angle of the lower footrest with respect to the upper footrest is maintained when the lower footrest is rotated by the arm portion.

7. A foot checkup device comprising:
   a motor unit;
   a footrest unit including a lower footrest configured to be rotated about a first rotation axis, an upper footrest configured to be rotated about a second rotation axis and a connecting member connecting the upper footrest and the lower footrest;
   a sensor unit configured to measure stiffness of a metatarsal joint of a user during the rotation of the upper footrest; and
   a coupling unit including an arm portion rotated by the motor unit and a rotary coupler coupled to the upper footrest,
   wherein the upper footrest is configured to be rotated by a predetermined angle about the second rotation axis by the rotation of the arm portion, and
   the lower footrest is configured not to be rotated about the first rotation axis by the rotation of the arm portion until the upper footrest is rotated by the predetermined angle.

8. The foot checkup device of claim 7, further comprising:
   a sensor unit configured to measure stiffness of an ankle joint of the user during the rotation of the lower footrest.

9. The foot checkup device of claim 7, further comprising:
an indenter rotatably supported by the connecting member between the upper footrest and the lower footrest.

10. The foot checkup device of claim 9, further comprising:
a sensor unit configured to measure stiffness of a sole of the user during the rotation of the indenter.

11. The foot checkup device of claim 7, wherein the lower footrest is rotated about the first rotation axis together with the upper footrest when the upper footrest is rotated.

12. A foot stiffness calculation method for calculating stiffness of a foot by using a foot stretching/checkup device that comprises a motor unit, a footrest unit including a lower footrest configured to be rotated about a first rotation axis, an upper footrest configured to be rotated about a second rotation axis and a connecting member connecting the upper footrest and the lower footrest, a sensor unit configured to measure stiffness of a metatarsal joint of a user during the rotation of the upper footrest, and a coupling unit including an arm portion rotated by the motor unit and a rotary coupler coupled to the upper footrest, wherein the upper footrest is configured to be rotated by a predetermined angle about the second rotation axis by the rotation of the arm portion, and the lower footrest is configured not to be rotated about the first rotation axis by the rotation of the arm portion until the upper footrest is rotated by the predetermined angle, the method comprising:

rotating the upper footrest about the second rotation axis; and calculating stiffness of a foot of a user based on a rotation angle and a torque of the upper footrest measured by a first sensor unit during the rotation of the upper footrest.

13. The foot stiffness calculation method of claim 12, further comprising:

rotating the lower footrest about the first rotation axis; and calculating the stiffness of the foot of the user based on a rotation angle and a torque of the lower footrest measured by a second sensor unit during the rotation of the lower footrest.

14. The foot stiffness calculation method of claim 12, wherein the foot stretching/checkup device further comprises an indenter rotatably supported by the connecting member between the upper footrest and the lower footrest, and further comprising:

rotating the indenter about a third rotation axis; and calculating the stiffness of the foot of the user based on a rotation angle and a torque of the indenter measured by an additional sensor unit during the rotation of the indenter.

* * * * *